United States Patent
Debbouz et al.

(10) Patent No.: US 8,389,504 B2
(45) Date of Patent: Mar. 5, 2013

(54) PRENATAL DIETARY SUPPLEMENT

(75) Inventors: Amar Debbouz, Newburgh, IN (US); Nagendra Rangavajla, Newburgh, IN (US); Zeina Jouni, Evansville, IN (US)

(73) Assignee: Mead Johnson Nutrition Company, Glenview, IL (US)

( * ) Notice: Subject to any disclaimer, the term of this patent is extended or adjusted under 35 U.S.C. 154(b) by 569 days.

(21) Appl. No.: 12/116,985

(22) Filed: May 8, 2008

(65) Prior Publication Data

US 2009/0281108 A1 Nov. 12, 2009

(51) Int. Cl.
*A61K 31/33* (2006.01)
*A61K 31/50* (2006.01)

(52) U.S. Cl. .................. 514/183; 514/249

(58) Field of Classification Search .......... 514/249
See application file for complete search history.

(56) References Cited

U.S. PATENT DOCUMENTS

| | | |
|---|---|---|
| 6,261,598 B1 | 7/2001 | Runge et al. |
| 6,368,621 B1 * | 4/2002 | Engel et al. .................. 424/451 |
| 6,509,029 B2 | 1/2003 | Runge et al. |
| 6,569,857 B1 | 5/2003 | Hermelin et al. |
| 6,576,253 B2 | 6/2003 | Manning et al. |
| 6,998,501 B1 | 2/2006 | Wright et al. |
| 7,056,525 B2 | 6/2006 | Runge et al. |
| 7,090,862 B2 | 8/2006 | Barrett-Reis et al. |
| 7,090,879 B2 | 8/2006 | Albrecht et al. |
| 2003/0104078 A1 | 6/2003 | Barrett-Reis et al. |
| 2003/0108594 A1 | 6/2003 | Manning et al. |
| 2005/0208179 A1 | 9/2005 | Albrecht et al. |
| 2006/0171993 A1 | 8/2006 | Barrett-Reis et al. |
| 2006/0210692 A1 | 9/2006 | Mower |
| 2006/0210697 A1 | 9/2006 | Mower |
| 2010/0028459 A1 * | 2/2010 | Kis .............................. 424/618 |

OTHER PUBLICATIONS

Gu et al., *Concentrations of Proanthocyanidins in Common Foods and Estimations of Normal Consumption*, J. Nutr., 134: 613-617, Mar. 2004.*
Lietz et al., *Xanthophyll and Hydrocarbon Carotenoid Patterns Differ in Plasma and Breast Milk of Women Supplemented with Red Palm Oil during Pregnancy and Lactation*, J. Nutr. 136:1821-1827, Jul. 2006.*
*DUET® DHA by StuartNatal®*, (2004) Xanodyne™ Pharmaceuticals, Inc., PI-845-A, May 2005.
*Citracal® Prenatal Rx*, Mission Pharmacal, Nov. 9, 2006 [Online] http://www.citracalprenatalrx.com/prescribe.jsp.
Drugs.com, *OptiNate Tablets*, Prescription Drug Information, Nov. 9, 2006, [Online] http://www.drugs.com/pdr/optinate_tablets.html.
Neuringer, M., et al., *Biochemical and functional effects of prenatal and postnatal ω3 fatty acid deficiency on retina and brain in rhesus monkeys*, Proc. Natl. Acad. Sci. USA, vol. 83 (Jun. 1986) p. 4021-4025.
*First Horizon Introduces OptiNate, a New Prenatal Vitamin With All-Natural, Vegetarian-Sourced Omega-3 Fatty Acids*, Nov. 9, 2006 [Online] http://www.npicenter.com/anm/templates/newsATemp.aspx?articleid=11960&zoneid=9.

* cited by examiner

*Primary Examiner* — Renee Claytor
(74) *Attorney, Agent, or Firm* — Waddey & Patterson, P.C.; James R. Cartiglia; Rebecca M. Barnett

(57) ABSTRACT

The present invention relates to a prenatal dietary supplement comprising at least one omega-3 fatty acid, at least one omega-6 fatty acid; folic acid; lutein; and at least one proanthocyanidin.

20 Claims, No Drawings

PRENATAL DIETARY SUPPLEMENT

BACKGROUND OF THE INVENTION

(1) Field of the Invention

The present invention relates generally to the field of prenatal dietary supplements.

SUMMARY OF THE INVENTION

Briefly, an embodiment of the invention is directed to a novel prenatal dietary supplement comprising at least one omega-3 fatty acid; at least one omega-6 fatty acid; folic acid; lutein; at least one carotenoid other than lutein; at least one polyphenol; and at least one flavonoid.

The invention is also directed, in an embodiment, to a novel prenatal dietary supplement comprising at least one omega-3 fatty acid; at least one omega-6 fatty acid; folic acid; lutein; and at least one proanthocyanidin.

In a separate embodiment, the invention is directed to a novel prenatal dietary supplement comprising DHA; ARA; folic acid; lutein; at least one carotenoid other than lutein; and at least one proanthocyanidin.

In yet another embodiment, the invention is directed to a novel prenatal dietary supplement comprising DHA; ARA; folic acid; lutein; at least one carotenoid other than lutein; and at least one polyphenol, wherein the supplement is in a form selected from the group consisting of a pill, tablet, capsule, liquid, liquid concentrate, and powder.

The invention is also directed, in several embodiments, to methods for preventing birth defects and enhancing brain, spine, or vision development in infants by administering the prenatal dietary supplement of the invention to pregnant mothers of those infants. In addition, the invention is directed to a method for increasing the concentration of Provitamin A in the breast milk of lactating mothers via the administration of the prenatal dietary supplement of the invention to lactating mothers.

DETAILED DESCRIPTION OF THE EMBODIMENTS

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment.

Thus, it is intended that the present invention covers such modifications and variations as come within the scope of the appended claims and their equivalents. Other objects, features and aspects of the present invention are disclosed in, or are obvious from, the following detailed description. It is to be understood by one of ordinary skill in the art that the present discussion is a description of exemplary embodiments only, and is not intended as limiting the broader aspects of the present invention.

In an embodiment, the invention is directed to a prenatal dietary supplement comprising at least one omega-3 fatty acid, at least one omega-6 fatty acid, folic acid, lutein, at least one carotenoid other than lutein, at least one polyphenol, and at least one flavonoid.

Generally speaking, omega-3 fatty acids are a family of polyunsaturated fatty acids which have a carbon-carbon double bond in the omega-3 position. Omega-3 fatty acids are important to human growth and development, but are not naturally synthesized by the body. Thus, omega-3 fatty acids must be obtained from foods or dietary supplements. The prenatal dietary supplement of the invention contains at least one omega-3 fatty acid. Any omega-3 fatty acid which is compatible with the prenatal dietary supplement may be used in this embodiment. In particular embodiments, the omega-3 fatty acid may be alpha-linolenic acid (ALA), eicosapentaenoic acid (EPA), docosahexaenoic acid (DHA), or combinations thereof.

In an embodiment of the present invention, the prenatal dietary supplement contains between about 100 and 1000 mg omega-3 fatty acids. In another embodiment of the invention, the prenatal dietary supplement contains between about 200 and 500 mg omega-3 fatty acids. In another embodiment of the invention, the prenatal dietary supplement contains between about 100 and 300 mg omega-3 fatty acids. In a particular embodiment, the prenatal dietary supplement contains about 250 mg omega-3 fatty acids. In another embodiment, the prenatal dietary supplement contains about 200 mg omega-3 fatty acids.

If the omega-3 fatty acid selected for the prenatal dietary supplement is DHA, DHA may be present in the supplement in an amount of at least 100 mg. In another embodiment, DHA may be present in the supplement in an amount of at least 200 mg. In yet another embodiment, DHA may be present in the supplement in an amount of between about 100 and 300 mg. In a particular embodiment, DHA may be present in the supplement in an amount of about 300 mg. In another embodiment, DHA may be present in the supplement in an amount of about 200 mg.

Similarly, omega-6 fatty acids are polyunsaturated fatty acids which have a carbon-carbon double bond in the omega-6 position. The prenatal dietary supplement of the invention contains at least one omega-6 fatty acid. Any omega-6 fatty acid which is compatible with the prenatal dietary supplement may be used in this embodiment. In a particular embodiment, the omega-6 fatty acid may be linoleic acid (LA), gamma-linolenic acid (GLA), eicosadienoic acid, dihomo-gamma-linolenic acid, docosadienoic acid, adrenic acid, docosapentaenoic acid, calendic acid, arachidonic acid (ARA), or combinations thereof. In a separate embodiment, the omega-6 fatty acid may be GLA, LA, ARA, or combinations thereof.

In an embodiment of the present invention, the prenatal dietary supplement contains between about 100 and 1000 mg omega-6 fatty acids. In another embodiment of the invention, the prenatal dietary supplement contains between about 200 and 500 my omega-6 fatty acids. In a particular embodiment, the prenatal dietary supplement contains about 250 mg omega-6 fatty acids.

If the omega-6 fatty acid selected for the prenatal dietary supplement is GLA, GLA may be present in the supplement in an amount of between about 10 mg and 100 mg. In another embodiment, the GLA in the composition is present in an amount ranging from about 100 mg to about 1,000 mg per 55 kg of body weight of the pregnant or lactating woman. While not wishing to be bound by the theory, the inventors believe that conversion of linoleic acid to GLA in the body is limited by various factors such as diet, health, age, and stress. Thus, the present invention, in an embodiment, provides supplemental GLA which may beneficially reduce inflammation, improve eczema, reduce dry eyes, decrease calcium loss in urine, and enhance calcium absorption.

If the omega-6 fatty acid selected for the prenatal dietary supplement is ARA, ARA may be present in the supplement in an amount of at least 10 mg. In another embodiment, ARA may be present in the supplement in an amount of at least 50 mg. In yet another embodiment, ARA may be present in the supplement in an amount of between about 100 and 500 mg. In a particular embodiment, ARA may be present in the supplement in an amount of about 300 mg. In another embodiment, ARA may be present in the supplement in an amount of about 500 mg.

In some embodiments, the prenatal nutritional supplement may have an omega-6:omega-3 fatty acid ratio of about 6:1 or less. In further embodiments, the prenatal nutritional supplement may have an omega-6:omega-3 fatty acid ratio in the range of between about 1:1 and 6:1, or between about 3:1 and about 6:1. In even further embodiments, the prenatal nutritional supplement may have an omega-6:omega-3 fatty acid ratio within the range of between about 5:1 and about 6:1. In still other embodiments, the prenatal nutritional supplement may have an omega-6:omega-3 fatty acid ratio of about 6:1. In still further embodiments, the prenatal nutritional supplement may have an omega-6:omega-3 fatty acid ratio of about 5:1.

The sources of the omega-3 and omega-s fatty acids can be any source known in the art such as marine oil, fish oil, single cell oil, egg yolk lipid, brain lipid, and the like. In some embodiments, the omega-3 and omega-6 fatty acids are sourced from the single cell Martek oil, DHASCO®, or variations thereof. The omega-3 and omega-6 fatty acids can be in natural form, provided that they do not result in any substantial deleterious effect on the infant. Alternatively, the omega-3 and omega-6 fatty acids can be used in refined form.

In addition to omega-3 and omega-6 fatty acids, the prenatal dietary supplement of the present invention may comprise folic acid in particular embodiments. Folic acid is a naturally-occurring water-soluble B-vitamin. Leafy vegetables, dried beans and peas, fortified cereal products, and some fruits are rich sources of folic acid. Biologically, folic acid is necessary for the production and maintenance of new cells. This is especially true during periods of rapid cell division and growth, such as infancy and pregnancy.

In an embodiment of the present invention, the prenatal dietary supplement contains between about 0.1 and 10 mg folic acid. In another embodiment of the invention, the prenatal dietary supplement contains between about 0.3 and 5 mg folic acid. In a particular embodiment, the prenatal dietary supplement contains between about 0.4 and 1 mg folic acid. In yet another embodiment, the prenatal dietary supplement contains between about 400 and 700 µg per day. In a particular embodiment, the prenatal dietary supplement contains about 600 µg per day.

In certain embodiments, the prenatal dietary supplement of the invention also may contain lutein. Lutein is one of over 600 naturally occurring carotenoids. It is found in green leafy vegetables such as spinach and kale and is employed by organisms as an antioxidant and for blue light absorption. In the body, lutein is concentrated in the macula, a small area of the retina responsible for central vision. It is believed that lutein protects the macula by filtering out potentially damaging forms of light.

In an embodiment of the invention, the prenatal dietary supplement contains between about 0.01 and 23 mg of lutein. In a separate embodiment, the prenatal dietary supplement contains between 1 and 10 mg of lutein. In another embodiment of the invention, the prenatal dietary supplement contains between about 0.1 and 5 mg of lutein. In yet another embodiment of the invention, the prenatal dietary supplement contains about 1 mg lutein.

In some embodiments of the invention, at least one carotenoid other than lutein may be incorporated into the prenatal dietary supplement. Carotenoids are a related group of more than 600 natural compounds, irrespective of geometric and stereoisomers, with demonstrated antioxidant efficacy. The carotenoids are broadly divided into "carotenes," or non-oxygen substituted hydrocarbon carotenoids, and "xanthophylls," oxygen-substituted carotenoids. Between 500 and 600 carotenoids have been identified, of which only about 24 occur in foods. The major carotenoids found in foods are a-carotene, β-carotene, lycopene, lutein, zeaxanthin, and β-cryptoxanthin. They are present in foods such as carrots, pumpkins, sweet potatoes, tomatoes, and other deep green, yellow, orange, red fruits and vegetables.

In an embodiment of the invention, the at least one carotenoid other than lutein may comprise a-carotene, β-carotene, lycopene, zeaxanthin, or β-cryptoxanthin. In an embodiment of the invention, the prenatal dietary supplement contains between about 0.01 and 10 mg of a carotenoid other than lutein. In an embodiment of the invention, the prenatal dietary supplement contains between about 0.1 and 5 mg of a carotenoid other than lutein. In an embodiment of the invention, the prenatal dietary supplement contains about 1 my of a carotenoid other than lutein.

In certain embodiments of the invention, the prenatal dietary supplement may contain at least one polyphenol. Polyphenols are a group of chemical substances found in plants and characterized by the presence of more than one phenol group per molecule. Dietary sources of polyphenols include berries, tea, beer, grapes/wine, olive oil, chocolate/cocoa, walnuts, peanuts, and other fruits and vegetables. Research indicates that polyphenols may have antioxidant characteristics with potential health benefits such as reducing the risk of cardiovascular disease or cancer. Polyphenols can be further subdivided into tannins, lignins, and flavonoids.

If included, the amount of polyphenol in an embodiment of the prenatal dietary supplement of the invention may be between about 10 and 400 mg. In another embodiment, the amount of polyphenol in the prenatal dietary supplement may be between about 50 and 250 mg. In yet another embodiment, the amount of polyphenol in the prenatal dietary supplement may be between about 100 and 200 mg.

In an embodiment of the invention, the prenatal dietary supplement may contain at least one flavonoid. Flavonoids are compounds found in fruits, vegetables, and certain beverages that have diverse beneficial biochemical and antioxidant effects. The antioxidant activity of flavonoids depends on their molecular structure. For example, the structural characteristics of certain flavonoids found in hops and beer confer surprisingly potent antioxidant activity which exceeds that of red wine, tea, or soy. Flavonoids are generally categorized according to their chemical structure into flavonols, flavones, flavonones, isoflavones, catchins, anthocyanidins, and chalcones. Flavonoids may help provide protection against the diseases by contributing to the total antioxidant defense system of the human body.

In some embodiments of the invention, the flavonoid may be selected from the group quercetin, xanthohumol, isoxanthohumol, proanthocyanidins, epicatechin, and genistein. If included, the amount of flavonoid in an embodiment of the prenatal dietary supplement of the invention may be between about 10 and 500 mg. In another embodiment, the amount of flavonoid in the prenatal dietary supplement may be between about 50 and 400 mg. In yet another embodiment, the amount of flavonoid in the prenatal dietary supplement may be between about 100 and 300 mg.

In a specific embodiment, the flavonoid selected may be proanthocyanidin. Proanthocyanidins can be found in many plants, most notably pine bark, grape seed, grape skin, and red wines of *Vitis vinifera*. Proanthocyanidins provide health benefits such as antioxidant protection against heart disease and cancer. If included, the amount of proanthocyanidin in an embodiment of the prenatal dietary supplement of the invention may be between about 10 and 500 mg. In another embodiment, the amount of proanthocyanidin in the prenatal dietary supplement may be between about 50 and 300 mg. In yet another embodiment, the amount of proanthocyanidin in the prenatal dietary supplement may be between about 100 and 200 mg.

The prenatal dietary supplement of the present invention may optionally include one or more of the following vitamins or derivatives thereof including, but not limited to, biotin, vitamin $B_1$, thiamin, thiamin pyrophosphate, vitamin $B_2$, riboflavin, flavin mononucleoride, flavin adenine dinucleotide, pyridoxine hydrochloride, thiamin mononitrate, folic acid, vitamin $B_3$, niacin, nicotinic acid, nicotinamide, niacinamide, nicotinamide adenine dinucleotide, tryptophan, biotin, pantothenic acid, vitamin $B_6$, vitamin $B_{12}$, cobalamin, methylcobalamin, deoxyadenosylcobalamin, cyanocobalamin, calcium pantothenate, pantothenic acid, vitamin C, ascorbic acid, vitamin A, retinol, retinal, retinoic acid, beta-carotene, vitamin D, vitamin $D_3$, calciferol, cholecalciferol, dihydroxy vitamin D, 1,25-dihydroxycholecalciferol, 7-dehyrdocholesterol, choline, vitamin E, vitamin E acetate, vitamin K, menadione, menaquinone, phylloquinone, naphthoquinone, and mixtures thereof.

The prenatal dietary supplement of the present invention may optionally include one or more of the following minerals or derivatives thereof, including, but not limited to, phosphorus, potassium, sulfur, sodium, docusate sodium, chloride, manganese, magnesium, magnesium stearate, magnesium carbonate, magnesium oxide, magnesium hydroxide, magnesium sulfate, copper, cupric sulfate, iodide, boron, zinc, zinc oxide, chromium, molybdenum, iron, carbonyl iron, ferric iron, ferrous fumarate, polysaccharide iron, fluoride, selenium, molybdenum, calcium phosphate or acetate, potassium phosphate, magnesium sulfate or oxide, sodium chloride, potassium chloride or acetate, ferric orthophosphate, alpha-tocopheryl acetate, zinc sulfate or oxide, copper gluconate, chromium chloride or picolonate, potassium iodide, sodium selenate, sodium molybdate, phylloquinone, cyanocobalamin, sodium selenite, copper sulfate, inositol, potassium iodide, cobalt, and mixtures thereof. Non-limiting exemplary derivatives of mineral compounds include salts, alkaline salts, esters and chelates of any mineral compound.

In an embodiment, the prenatal dietary supplement of the invention is designed to be consumed by pregnant women, women that are lactating or breastfeeding, or women that are trying to become pregnant.

The prenatal dietary supplement of the invention may be administered in one or more doses daily. In some embodiments, the prenatal dietary supplement is administered in two doses daily. In a separate embodiment, the prenatal dietary supplement is administered in three daily doses.

Any orally acceptable dosage form is contemplated by the invention. Examples of such dosage forms include, but are not limited to pills, tablets, capsules, liquids, liquid concentrates, powders, elixirs, solutions, suspensions, emulsions, lozenges, beads, cachets, and combinations thereof. Alternatively, the prenatal dietary supplement of the invention may be added to a more complete nutritional product. In this embodiment, the nutritional product may contain protein, fat, and carbohydrate components and may be used to supplement the diet or may be used as the sole source of nutrition.

Studies have previously linked an increased incidence of birth defects with inadequate maternal nutrition during pregnancy. Thus, in certain embodiments, the invention comprises a method for preventing birth defects in infants comprising administering the prenatal dietary supplement described herein. The invention also comprises a method for enhancing brain, spine, or vision development in infants by administering the prenatal dietary supplement of the invention to pregnant mothers of those infants. It is believed that the specific combinations of the ingredients in the invention provide a synergistic effect and may thereby enhance brain, spine, or vision development.

In yet another embodiment of the invention, the method involves enhancing the antioxidant and nutritional properties of breast milk in lactating mothers via the administration of the prenatal dietary supplement of the present invention. In certain embodiments, the prenatal dietary supplement of the invention may increase the concentration of Provitamin A in the breast milk of lactating mothers. In a particular embodiment, the administration of beta-carotene may increase the concentration of Provitamin A in the breast milk of lactating mothers.

In other embodiments, the invention is directed to a method of preventing chromosomal mutations in an infant via the administration of the prenatal dietary supplement of the present invention to pregnant mothers of those infants. In this embodiment, the prenatal dietary supplement has anti-mutagenic activity.

The invention is also directed to a method for strengthening the blood vessels of an infant, including those in the heart, lung and brain via the administration of the prenatal dietary supplement of the present invention to pregnant mothers of those infants. In this embodiment, the strengthened blood vessels may improve delivery of oxygen to the cells and maintain overall health for both pregnant mothers and their infants.

During pregnancy, an increase in caloric intake will often increase reactive oxygen species (ROS) production, thereby increasing oxidative damage. Another embodiment of the invention is directed to a method of lowering the oxidative damage associated with the increase in ROS production in pregnant women via administration of the prenatal dietary supplement of the present invention.

In still a further embodiment, the invention is directed to a method for decreasing inflammation throughout a prenatal subject's body comprising administering the prenatal dietary supplement to the subject. In another embodiment, the invention is directed to a method for minimizing the oxidation of human milk nutrients via the administration of the prenatal dietary supplement of the present invention to prenatal women. The human milk nutrients may be selected from the group consisting of antioxidants, LCPUFA, lipids, amino acids, proteins, and combinations thereof.

The invention is also directed to a method for strengthening bone formation in infants and/or pregnant women via the administration of the prenatal dietary supplement of the present invention to prenatal women. While not wishing to be bound by this or any theory, it is believed that the prenatal dietary supplement of the invention may strengthen bone formation via collagen stabilization and/or production.

In still another embodiment, the invention is directed to a method of enhancing skin elasticity in infants and/or pregnant women via the administration of the prenatal dietary supplement of the present invention to prenatal women. While not wishing to be bound by this or any theory, it is believed that the skin elasticity is enhanced via elastin stabilization and/or production.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties to the extent that they do not contradict anything contained herein.

The discussion of the references herein is intended merely to summarize the assertions made by their authors and no admission is made that any reference constitutes prior art. Applicants reserve the right to challenge the accuracy and pertinence of the cited references.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. A method for enhancing the development of an organ selected from the group consisting of the brain and spine in an infant comprising administering a prenatal dietary supplement to a pregnant mother of the infant, wherein the prenatal dietary supplement comprises at least one omega-3 fatty acid, at least one omega-6 fatty acid, folic acid, lutein, between 50 and 300 mg of at least one proanthocyanidin, and an additional polyphenol.

2. A method for enhancing the development of an organ selected from the group consisting of the brain and spine in a breastfed infant comprising administering a dietary supplement to a lactating mother of the infant, wherein the dietary supplement comprises at least one omega-3 fatty acid, at least one omega-6 fatty acid, folic acid, lutein, between 50 and 300 mg of at least one proanthocyanidin, and an additional polyphenol.

3. The method of claim 1, wherein the prenatal dietary supplement comprises between about 400 and 700 µg folic acid.

4. The method of claim 1, wherein the prenatal dietary supplement comprises between about 1 and 10 mg of lutein.

5. The method of claim 1, wherein the prenatal dietary supplement further comprises an additional carotenoid.

6. The method of claim 1, wherein the prenatal dietary supplement comprises between about 50 and 250 mg polyphenol.

7. The method of claim 1, wherein the prenatal dietary supplement further comprises an additional flavonoid.

8. The method of claim 1, wherein the prenatal dietary supplement comprises between about 100 and 300 mg omega-3 fatty acids.

9. The method of claim 1, wherein the omega-3 fatty acid comprises docosahexaenoic acid.

10. The method of claim 1, wherein the prenatal dietary supplement comprises between about 100 and 500 mg omega-6 fatty acids.

11. The method of claim 1, wherein the prenatal dietary supplement is in a form selected from the group consisting of a pill, a tablet, a capsule, a liquid, a liquid concentrate, and a powder.

12. The method of claim 2, wherein the dietary supplement comprises between about 400 and 700 µg folic acid.

13. The method of claim 2, wherein the dietary supplement comprises between about 1 and 10 mg of lutein.

14. The method of claim 2, wherein the dietary supplement further comprises an additional carotenoid.

15. The method of claim 2, wherein the dietary supplement comprises between about 50 and 250 mg polyphenol.

16. The method of claim 2, wherein the dietary supplement further comprises an additional flavonoid.

17. The method of claim 2, wherein the dietary supplement comprises between about 100 and 300 mg omega-3 fatty acids.

18. The method of claim 2, wherein the omega-3 fatty acid comprises docosahexaenoic acid.

19. The method of claim 2, wherein the dietary supplement comprises between about 100 and 500 mg omega-6 fatty acids.

20. The method of claim 2, wherein the dietary supplement is in a form selected from the group consisting of a pill, a tablet, a capsule, a liquid, a liquid concentrate, and a powder.

* * * * *